(12) United States Patent
Piantoni et al.

(10) Patent No.: US 12,350,132 B2
(45) Date of Patent: Jul. 8, 2025

(54) LINE AND PROCESS FOR THE PRODUCTION OF NAPPY PANTS

(71) Applicant: GDM S.p.A., Bologna (IT)

(72) Inventors: Matteo Piantoni, Bologna (IT); Alessandro Zavalloni, Bologna (IT)

(73) Assignee: GDM S.p.A., Bologna (IT)

( * ) Notice: Subject to any disclaimer, the term of this patent is extended or adjusted under 35 U.S.C. 154(b) by 107 days.

(21) Appl. No.: 17/838,468

(22) Filed: Jun. 13, 2022

(65) Prior Publication Data

US 2022/0395406 A1 Dec. 15, 2022

(30) Foreign Application Priority Data

Jun. 15, 2021 (IT) .................. 102021000015557

(51) Int. Cl.
| | |
|---|---|
| *A61F 13/15* | (2006.01) |
| *A61F 13/49* | (2006.01) |
| *A61F 13/496* | (2006.01) |
| *A61F 13/539* | (2006.01) |

(52) U.S. Cl.
CPC .. *A61F 13/15772* (2013.01); *A61F 13/49011* (2013.01); *A61F 13/496* (2013.01); *A61F 13/539* (2013.01)

(58) Field of Classification Search
CPC .......... A61F 13/15772; A61F 13/49011; A61F 13/496; A61F 13/539
See application file for complete search history.

(56) References Cited

U.S. PATENT DOCUMENTS

| | | | | |
|---|---|---|---|---|
| 2003/0004594 | A1* | 1/2003 | Liu | ................. B32B 39/00 700/95 |
| 2016/0136004 | A1* | 5/2016 | LaVon | ............. A61F 13/15772 604/366 |
| 2018/0353348 | A1* | 12/2018 | Kawka | ...................... G06T 7/97 |

OTHER PUBLICATIONS

Italian Search Report dated Mar. 10, 2022 from counterpart Italian Patent Application No. IT102021000015557.

\* cited by examiner

*Primary Examiner* — Daniel McNally
(74) *Attorney, Agent, or Firm* — SHUTTLEWORTH & INGERSOLL, PLC; Timothy J. Klima

(57) ABSTRACT

A line for the production of diaper pants including at least one absorbent pad and a plurality of elastic bands, forming a pants-like structure; the production line includes a first forming unit for forming a composite web from which said absorbent pads are obtained, a second unit for forming elastic bands for forming said elastic bands and an assembly line for assembling the pads and the elastic bands to construct the diaper pants; the assembly line includes a plurality of processing units, each including a computerized command and control unit and a computerized high level control unit in communication with the computerized command and control units in the assembly line; the high level control unit is configured to impart to each computerized command and control unit at least one control signal for the respective processing unit as a function of the size of the diaper pants being produced in the production line.

10 Claims, 3 Drawing Sheets

LINE AND PROCESS FOR THE PRODUCTION OF NAPPY PANTS

This application claims priority to Italian Patent Application IT102021000015557 filed Jun. 15, 2021, the entirety of which is incorporated by reference herein.

BACKGROUND OF THE INVENTION

This invention relates to a line and a process for the production of diaper pants.

Lines for the production of diapers, and in particular, of diaper pants, are made up of a multitude of operating stations and units which, starting from the raw materials, continuously perform successive and/or parallel processes to obtain finished products that are suitably positioned, folded and ready for packaging.

With reference to FIG. 2, it may be observed that a pair of diaper pants, once formed, can be schematized as two rectangles, orthogonal to each other and at least partly intersecting.

The diaper has, amongst others, four characteristic dimensions A, B, C and D which are respectively, with reference to FIG. 2, the width of the elastic bands in the waist, the height of the elastic bands in the waist, the length of the absorbent pad and the width of the absorbent pad; in the product, the absorbent pad is obviously two times C in length because, in the illustration, the pad is folded in half.

The processing units of the production line are each structured to handle the product and the semi-products which, as they advance along the line, progressively form the end product.

In particular, each processing unit must be configured to adapt to at least one of the above mentioned four dimensions A, B, C and D for each diaper size being produced.

When the size of the diaper or of one of its components has to be changed, hence when at least one of those dimensions changes, the processing units must generally be adjusted or modified to be able to handle the dimensions of the new size.

More precisely, it is necessary to make macro-adaptations or macro-adjustments, together with micro-adaptations or micro-adjustments affecting minor aspects of the line.

By way of non-limiting example, the following macro-adjustments may be necessary: replacing the absorbent pad cutting unit as a function of the dimension C of the pads; replacing the absorbent pad stepper positioning unit when the dimension A of the elastic bands changes; replacing the cutting means or varying the diameter of the cutting means based on cutting and shaping requirements as a function of A, B and C; replacing the label applicator or varying its diameter as a function of A; replacing, or changing the diameter of the welding unit for welding the elastic bands in the waist based on dimension A; modifying or replacing the product orienting and spacing units based on dimensions A, B, C.

In addition to all these and other adjustments that must be carried out on the line when product size changes, the Applicant has noticed that prior art lines are unable to continuously cover all the possible sizes, from the smallest to the largest, but only some of the sizes in the range from the smallest to the largest, based on design choices.

The Applicant has thus observed that in the relevant technical sector, there remains a need for a line for the production of diapers, and in particular, of diaper pants, capable of making products, as required, in any size after just some quick and relatively simple adjustments.

SUMMARY OF THE INVENTION

In this context, our intention is to propose a line and a process for the production of diaper pants capable of overcoming at least some of the drawbacks of the prior art and of meeting the above mentioned need.

One aim of this invention is to provide a line and a process for the production of diaper pants to allow making any product size, even to meet market demand for increasingly customized products.

One aim of this invention is to provide a line for the production of diaper pants to allow adapting the line in a practical manner (for example, automated or by replacing and/or adjusting at least one mechanical part) to make the product in any size, at least as regards the macro-adjustments necessary for size changeover.

These aims are achieved by a line and a process for the production of diaper pants comprising the technical features described in one or more of the accompanying claims. The dependent claims correspond to possible different embodiments of the invention.

According to an aspect, this disclosure regards a line for the production of diaper pants of the type each comprising at least one absorbent pad and a plurality of elastic bands.

Once assembled, the elastic bands and the absorbent pads form the pant structure that identifies the type of product concerned.

The production line comprises a forming unit for forming a composite web from which the absorbent pads are obtained. The composite web is for example made up of a topsheet, a backsheet and an absorbent structure sandwiched between the two.

The production line comprises an elastic band forming unit for forming the elastic bands.

The production line comprises an assembly line which has an infeed for a composite web, an infeed for elastic bands and an outfeed for the diaper pants produced.

According to an aspect of the disclosure, the assembly line comprises a plurality of processing units to construct the diaper pants from at least one composite web and elastic bands.

According to an aspect, the processing units each comprise a computerized command and control unit and the production line comprises a computerized high level control unit in communication with the computerized command and control units of the processing units.

According to an aspect, each processing unit is provided with a respective computerized command and control unit and all the computerized command and control units are controlled, directly or indirectly, by the high level control unit.

According to an aspect, the high level control unit is configured to impart at least one respective control signal to each computerized command and control unit.

According to an aspect, each control signal is a function of the size of the diaper pants being produced in the production line.

The processing units are each configured to perform a respective step of processing as a function of the size set using the respective control signal.

Advantageously, the production line is able to make diaper pants of any size of all the possible sizes and adapting the processing unit to a different size is automated on the basis of the commands imparted by a single high level control unit which sends the control signals to each single processing unit.

The control signals are a function of the size and each processing unit adapts to the new size thanks to its own local command and control unit.

According to an aspect, at least one control signal generated by the high level control unit is a function of the width of the absorbent pad.

According to an aspect, at least one control signal generated by the high level control unit is a function of the length of the absorbent pad.

According to an aspect, at least one control signal generated by the high level control unit is a function of the width of an elastic band in the waist of the diaper pants.

According to an aspect, at least one control signal generated by the high level control unit is a function of the height of an elastic band in the waist of the diaper pants.

According to an aspect, the production line comprises a processing unit which comprises a cutting device for cutting the composite web to obtain a succession of absorbent pads. The cutting device preferably comprises at least one cutter driven by the computerized command and control unit of the processing unit.

Preferably, the cutter is actuated according to an electronic cam profile based on a control signal.

The control signal is generated by the high level control unit as a function of the length of the absorbent pad. The electronic cam profile, that is an electronic cam drive of the cutter, allows meeting all requirements regarding size, since it can cut the web into pieces of any length.

According to an aspect, the production line comprises a processing unit that comprises a turning and spacing device to space and turn the absorbent pads of a succession of absorbent pads.

According to an aspect, the turning and spacing device comprises at least one rotary pickup means for picking up an absorbent pad and a movement system for moving the pickup means.

The movement system is driven by the computerized command and control unit of the processing unit and is actuated according to an electronic cam profile based on a control signal received from the processing unit.

The control signal is generated by the high level control unit as a function of the width of an elastic band in the waist of the diaper pants.

The processing unit can thus advantageously adapt to any size of absorbent pad, picking it up at one spacing and depositing it at another.

According to an aspect, the production line may comprise a single processing unit that not only cuts the composite web but also spaces, repositions and orients the absorbent pads.

According to an aspect, the movement system may comprise at least one linear motor.

According to an aspect, the production line comprises a processing unit that comprises a cutting device to at least partly cut the elastic bands in a coupling zone where the elastic bands are coupled to a corresponding absorbent pad.

According to an aspect, the cutting device comprises at least one cutter driven by the computerized command and control unit of the processing unit.

According to an aspect, the cutter is actuated according to an electronic cam profile based on a respective control signal.

The control signal is generated by the high level control unit as a function of the width of an elastic band in the waist of the diaper pants and/or of the width of the absorbent pad.

Advantageously, the cutter, being actuated by an electronic cam, can execute any command from the high level control unit, based on the size of the diaper pants.

According to an aspect, the production line comprises a processing unit that comprises a cutting device for at least partly shaping the elastic bands, for example, at the joining zone where the absorbent pad and the elastic bands of the diaper pants are joined.

According to an aspect, the cutting device is a laser or waterjet cutting device and is driven by the computerized command and control unit of the processing unit based on a control signal generated by the high level control unit as a function of the length of the absorbent pad and/or as a function of the width of an elastic band in the waist of the diaper pants and/or as a function of the height of the elastic band in the waist of the diaper pants.

According to an aspect, the production line comprises a processing unit that comprises an applicator which applies a label to each pair of diaper pants.

According to an aspect, the applicator is driven according to an electronic cam profile based on a control signal.

The control signal is generated by the high level control unit as a function of the width of an elastic band in the waist of the diaper pants.

Advantageously, the applicator, being actuated by an electronic cam, can execute any command from the high level control unit, based on the size of the diaper pants so that the label is positioned correctly according to the size.

According to an aspect, the production line comprises a processing unit that comprises a welding device for welding the elastic bands in the waist of the diaper pants.

According to an aspect, the welding device comprises a plurality of welding units which are spaced along the feed path of the diaper pants to be formed as a function of the width of an elastic band in the waist of the diaper pants.

According to an aspect, the welding units are positioned relative to each other, along the feed path, by the computerized command and control unit of the processing unit, based on a control signal.

According to an aspect, the control signal is generated by the high level control unit as a function of the width of an elastic band in the waist of the diaper pants.

That way, based on the width of the elastic bands in the waist of the diaper, the welding units are positioned as a function of the weld pitch to be obtained.

According to an aspect, the production line comprises a welding device for welding the elastic bands in the waist of the diaper pants and which comprises at least one welder.

According to an aspect, the welder is driven by the computerized command and control unit of the processing unit and is actuated according to an electronic cam profile based on a control signal.

The control signal is generated by the high level control unit as a function of the width of an elastic band in the waist of the diaper pants.

Advantageously, the use of one or more electronic cam welders allows adapting to the welded product spacing variations due to product size changeover.

According to an aspect, the production line comprises a processing unit that comprises a cutting device for separating each pair of diaper pants from a succession of diaper pants that are joined to each other.

According to an aspect, the cutting device comprises a cutter driven by the computerized command and control unit of the processing unit and is actuated according to an electronic cam profile based on a control signal.

The control signal is generated by the high level control unit as a function of the width of an elastic band in the waist of the diaper pants. Advantageously, the cutting device actuated by an electronic cam allows cutting the diaper pants from the succession of diaper pants in any size.

According to an aspect, the production line comprises a processing unit that comprises a turning and spacing device for turning and spacing the diaper pants of a succession of diaper pants.

The turning and spacing device comprises at least one diaper pants pickup means driven by the computerized command and control unit of the processing unit.

According to an aspect, the pickup means is actuated according to an electronic cam profile based on a control signal generated by the high level control unit as a function of the width of an elastic band in the waist of the diaper pants, which determines the pickup spacing of the diaper pants.

According to an aspect, the control signal is a function of the height of the elastic band in the waist of the diaper pants and of the length of the absorbent pad, which determine, for example, the spacing at which the diaper pants are released.

According to an aspect, the production line comprises a processing unit that comprises a folding device for folding an elastic band in the waist of the diaper pants. The folding device is actuated on the basis of a control signal that is generated by the high level control unit as a function of the width of an elastic band in the waist of the diaper pants and/or of the width of the absorbent pad.

According to an aspect, the folding device is what is known as an active device and is configured to work on an elastic band of any width in the waist of the diaper pants and/or on an absorbent pad of any width.

According to an aspect, the production line comprises a processing unit that comprises a folding device for folding at least the absorbent pad of the diaper pants along a folding line transverse to the absorbent pad.

The folding device is actuated on the basis of a control signal that is generated by the high level control unit as a function of the height of an elastic band in the waist of the diaper pants and/or of the length of the absorbent pad.

According to an aspect, this disclosure relates to a process for the production of diaper pants of the type each comprising at least one absorbent pad and a plurality of elastic bands; the elastic bands and the absorbent pad schematically form a pants-like structure.

According to an aspect, the process comprises a step of forming a composite web to form a composite web from which the absorbent pads will be obtained and a step of forming elastic strips to form the elastic bands.

The process comprises a plurality of steps of processing the composite web, the elastic bands and semi-products derived from the composite web, from the elastic bands or from combinations thereof during processing.

According to an aspect, the process comprises a step of generating, for each processing step, at least one respective control signal as a function of the size of the diaper pants being produced.

According to an aspect, the process comprises a step of adapting each processing step to the size of the diaper pants being produced as a function of the respective control signal.

Advantageously, based on the size to be produced, a respective control signal is generated for each processing step so that each step adapts to the size being produced, that is to say, to the dimensions of the diaper pants to be obtained.

According to an aspect, at least one control signal is generated as a function of the width of the absorbent pad.

According to an aspect, at least one control signal is generated as a function of the length of the absorbent pad.

According to an aspect, at least one control signal is generated as a function of the width of an elastic band in the waist of the diaper pants.

According to an aspect, at least one control signal is generated as a function of the height of an elastic band in the waist of the diaper pants.

According to an aspect, the production process comprises a step of cutting the composite web to obtain a succession of absorbent pads.

The step of cutting is based on a control signal generated as a function of the length of the absorbent pad.

According to an aspect, the production process comprises a step of turning and spacing to space and turn the absorbent pads of a succession of absorbent pads. The step of turning and spacing is based on a control signal generated as a function of the width of an elastic band in the waist of the diaper pants.

In effect, the absorbent pads are advantageously positioned as a function of the spacing they are required to have after the step of turning and spacing for any product size.

According to an aspect, the production process comprises a step of cutting to at least partly cut the elastic bands in a coupling zone where the elastic bands are coupled to the respective absorbent pad.

The step of cutting is based on a control signal generated as a function of the width of an elastic band in the waist of the diaper pants corresponding to a position of the absorbent pad.

According to an aspect, the production process comprises a step of cutting to at least partly shape the elastic bands of the diaper pants.

The step of cutting is based on a control signal generated as a function of the length of the absorbent pad and/or as a function of the width of an elastic band in the waist of the diaper pants and/or as a function of the height of the elastic band in the waist of the diaper pants.

According to an aspect, the step of cutting to at least partly shape the elastic bands of the diaper pants comprises a step of laser cutting and/or a step of waterjet cutting.

According to an aspect, the production process comprises a step of applying a label to each pair of diaper pants.

The step of applying is based on a control signal generated as a function of the width of an elastic band in the waist of the diaper pants.

According to an aspect, the production process comprises a step of welding the elastic bands in the waist of the diaper pants by means of a plurality of welding units.

According to an aspect, the step of welding comprises a step of spacing the welding units along a feed path of the diaper pants to be formed.

According to an aspect, the step of spacing is based on a control signal generated as a function of the width of an elastic band in the waist of the diaper pants.

According to an aspect, the production process comprises a step of cutting to separate each pair of diaper pants from a succession of diaper pants that are joined to each other in a continuous web.

The step of cutting is based on a control signal generated as a function of the width of an elastic band in the waist of the diaper pants.

According to an aspect, the production process comprises a second step of turning and spacing to turn and space the diaper pants of a succession of diaper pants.

The second step of turning and spacing is based on a control signal generated as a function of the width of an elastic band in the waist of the diaper pants and of the height of the elastic band in the waist of the diaper pants.

According to an aspect, the production process comprises a step of folding to fold at least one elastic band in the waist of the diaper pants. The step of folding is based on a control signal generated as a function of the width of an elastic band in the waist of the diaper pants and/or of the width of the absorbent pad.

According to an aspect, the production process comprises a step of folding to fold the absorbent pad of the diaper pants along a folding line transverse to the absorbent pad.

The step of folding is based on a control signal generated as a function of the height of an elastic band in the waist of the diaper pants and/or of the length of the absorbent pad.

BRIEF DESCRIPTION OF THE DRAWINGS

Further features and advantages are more apparent in the exemplary, hence non-limiting description which follows of a preferred but non-exclusive embodiment of a line and a process for the production of diaper pants.

The description is set out below with reference to the accompanying drawings which are provided solely for purposes of illustration without restricting the scope of the invention and in which.

DESCRIPTION OF THE PREFERRED EMBODIMENTS

Figure 1:
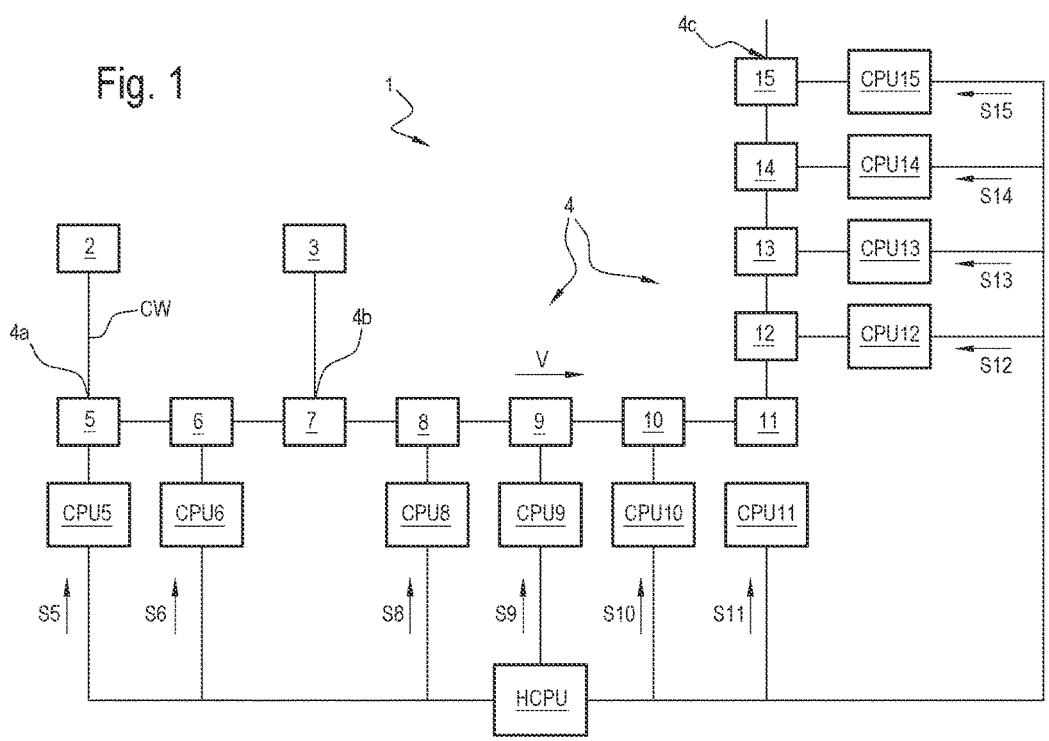
FIG. 1 shows a schematic block diagram representing production line according to the disclosure.
Figure 4:
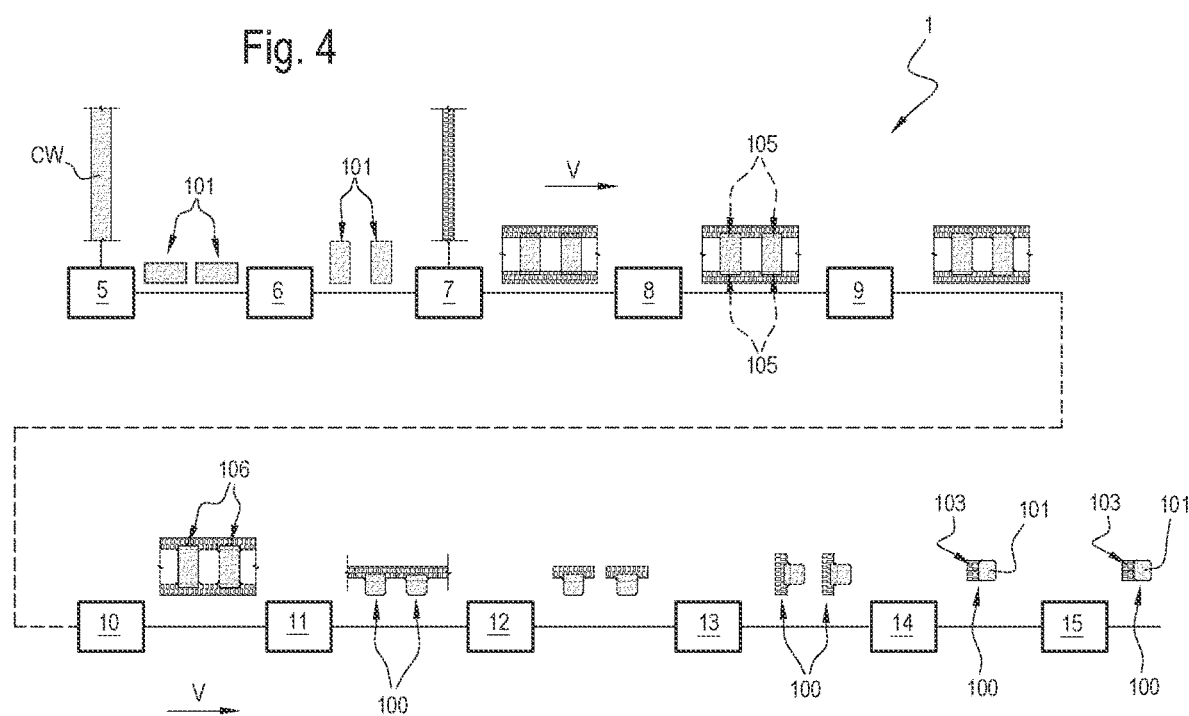
FIG. 4 shows a production line according to the disclosure in a schematic block diagram, with some parts removed and with a schematic visual indication of the processing steps.

With reference to FIGS. 1 and 4, the numeral 1 denotes a production line according to this disclosure.

Figure 2:
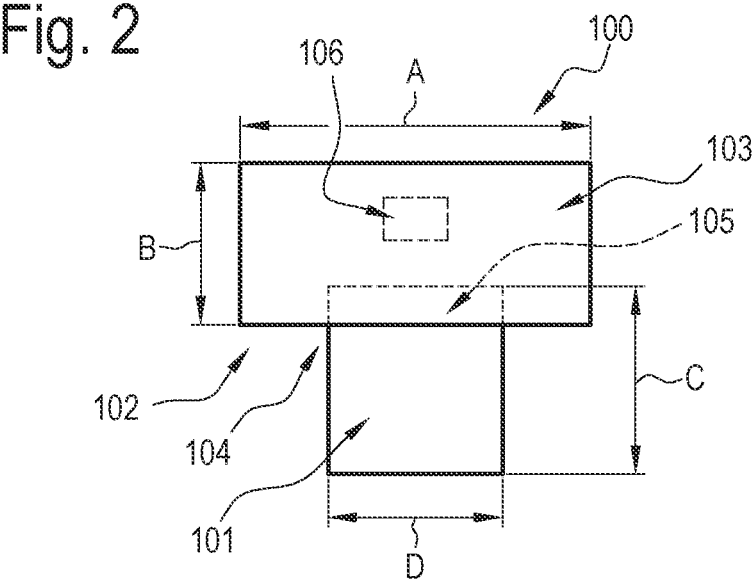
FIG. 2 shows a schematic plan view of a pair of diaper pants.

The production line 1 is intended for the production of diaper pants of the type represented schematically in FIG. 2.

With reference to FIG. 2, the numeral 100 denotes a pair of diaper pants of substantially known type, described only insofar as necessary for understanding this invention.

The diaper 100 essentially comprises an absorbent pad 101 and an elastic structure 102 for supporting the pad 101.

The elastic structure 102 allows the diaper to be worn like a pair of pants by a user not illustrated.

The absorbent pad 101 essentially comprises a topsheet, a backsheet and an absorbent pad sandwiched between the two and obtained, as explained below, from a composite web CW.

The structure 102 is formed of elastic bands 103, 104 that comprise webs of non-woven fabric between which elastics are inserted.

The structure 102 essentially comprises an elastic ring that defines the waist 103 of the diaper 100 and a pair of elastic rings 104 that define the openings for the user's legs. The elastic ring 103 and the rinds 104 are formed of elastic bands 103, 104.

The diaper 100 has, amongst others, four characteristic dimensions A, B, C and D which, with reference to FIG. 2, are the width of the elastic bands in the waist or waist 103, the height of the elastic bands in the waist or waist 103, the length of the absorbent pad 101 folded in half and the width of the absorbent pad 101, respectively.

For simplicity, the full length of the pad 101 is hereinafter represented by the dimension 2C.

Figure 3:
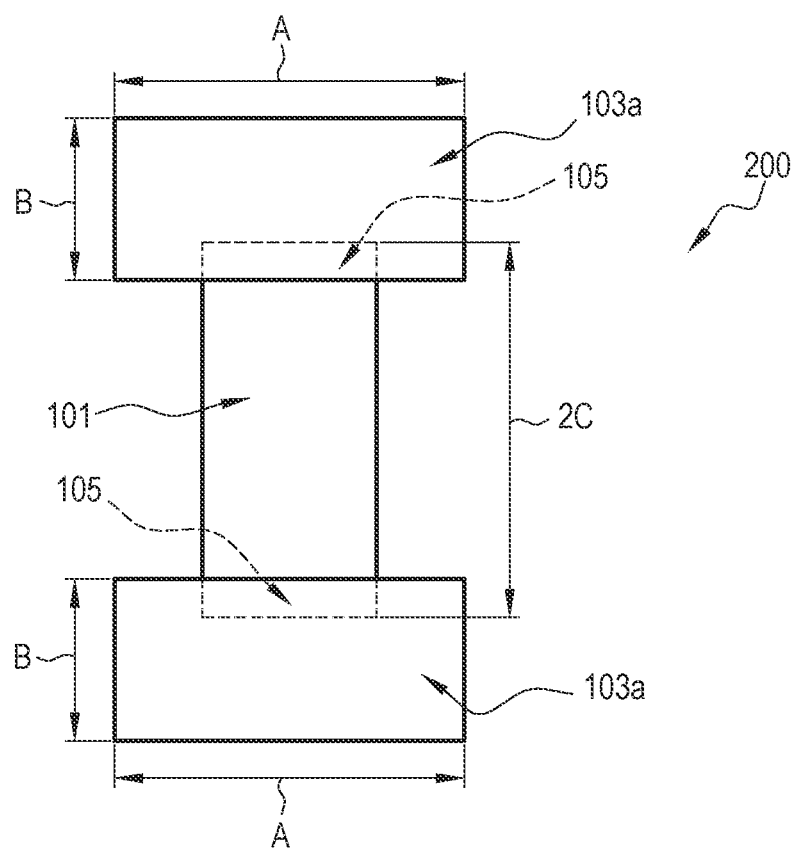
FIG. 3 shows a schematic plan view of a semi-product used for the production of a pair of diaper pants.

The reference numeral 200 in FIG. 3 denotes a semi-product from which the diaper 100 is obtained; the semi-product 200 is commonly called H product on account of its shape. The semi-product 200 has two elastic bands 103a, 103b joined by the absorbent pad 101 stretched out flat.

When the pad 101 is folded, the elastic bands 103a, 103b are welded to each other to form the waist 103 of the diaper 100.

In the embodiment illustrated, the production line 1 comprises a forming unit 2 for forming the composite web CW from which, as mentioned, the pads 101 are obtained.

The production line 1 comprises a forming unit 3 for forming elastic bands 103, 104 to form the elastic bands 103, 104 that are intended, for example, to form the structure 102.

The line 1 comprises an assembly line 4 having an infeed 4a for the composite web CW formed by the unit 2 and an infeed 4b for the elastic bands 103, 104 formed by the unit 3.

The assembly line 4 has an outfeed 4c for the diaper pants 100 made.

The assembly line 4 comprises a plurality of processing units to construct the diaper pants 100 at least from the composite web CW and the elastic bands 103, 104.

The production line 1, and in particular the assembly line 4, comprises the processing units disposed in sequence along a path for the production of the diapers 100.

The term "processing units" is used to denote working units which perform macroscopic operations in the process of manufacturing the diapers 100 and which must be adapted, in their functional parameters, to the characteristic dimensions of the diaper 100 of the size being made.

In a preferred embodiment, each processing unit comprises a computerized command and control unit which controls the operation of the respective processing unit.

The production line 1 comprises a computerized high level control unit HCPU in communication with the computerized command and control units in the assembly line 4.

The high level control unit HCPU is configured to impart to each computerized command and control unit at least one control signal for the respective processing unit as a function of the size of the diaper pants 100 being produced in the production line 1. The size, or type, of diaper 100 produced is imparted to the production line 1 by a line manager.

As will become clearer below, the processing units are each configured to perform a respective process as a function of the size imparted through the respective control signal.

In practice, changing the size of the diaper 100 being produced is managed by the HCPU, which drives the command and control units so they adapt the respective processing units to the new size.

Advantageously, the processing units do not require macroscopic mechanical interventions such as, for example, replacement of rotary knives, replacement of wheels with wheels of different diameter, modification of conveyor belts.

That way, interventions on the production line and line downtime are minimized and the time can be used for minor adjustments, for example, modifications to glue dispensers or adjustments to web tension devices, which are in any case inevitable when changing over to a different size.

In an embodiment, at least one control signal generated by the HCPU is a function of the width D of the absorbent pad 101.

In an embodiment, at least one control signal generated by the HCPU is a function of the length 2C of the absorbent pad 101.

In an embodiment, at least one control signal generated by the HCPU is a function of the width A of the elastic band 103.

In an embodiment, at least one control signal generated by the HCPU is a function of the height B of the elastic band 103.

The processing units of the assembly line 4 comprise a first processing unit 5 for cutting the composite web CW and provided with its own computerized command and control unit CPU5.

The processing unit 5 comprises a cutting device, not illustrated, for cutting the composite web to obtain a succession of absorbent pads 101.

The cutting device of the processing unit 5 comprises at least a first cutter, driven by the unit CPU5 and actuated according to an electronic cam profile based on a first control signal 35.

The signal S5 is generated by the control unit HCPU as a function of the length of the absorbent pad 101.

In practice, the cutter, movable by the electronic cam, can cut the composite web CW into pieces that define absorbent pads 101 of the required length based on the size of the diaper 100 being produced and based on the commands of the HCPU.

The processing unit 5 allows the length C of the absorbent pad 101 to be adjusted automatically.

The production line 1, in particular the assembly line 4, comprises a second processing unit 6, provided with its own computerized command and control unit CPU6, for spacing and rotating the absorbent pads 101 of a succession of absorbent pads leaving the processing unit 5.

The processing unit 6 is located downstream of the processing unit 5 in a production feed direction V of the diapers 100.

The processing unit 6 comprises a turning and spacing device of substantially known type and not illustrated.

For example, in an embodiment, the turning and spacing device comprises at least one rotary pickup means for picking up an absorbent pad 101, and a motor, for example, a linear motor, for moving the pickup means.

The turning and spacing device, in particular the linear motor, is driven by the computerized command and control unit CPU6 of the processing unit 6 and is actuated according to an electronic cam profile based on a control signal S6.

The control signal S6 is generated by the control unit HCPU as a function of the width A of the waist 103 of the size of the diaper 100 being produced.

That way, the absorbent pads 101 are positioned according to how they are to be coupled to the corresponding elastic bands 103, 104.

In practice, the processing unit 6 allows picking up the absorbent pads 101 based on their length C, which varies continually as a function of the size, and placing the absorbent pads 101 on the elastic bands 103, 104, whose length A, in the finished product, varies continually as a function of the size of the diaper 100, The processing unit 6 allows picking up the absorbent pads 101 according to one spacing which varies on the basis of the size and places them according to another spacing, also variable on the basis of the size of the diaper 100.

The processing units of the production line 1 comprise a processing unit 7, of substantially known type, for coupling the elastic bands 103, 104 to the absorbent pads 101. In practice, the processing unit 7 defines a coupling station with semi-products 200 moving along downstream of it in uninterrupted succession.

In an embodiment, the processing units of the production line 1 comprise a third processing unit 8, provided with its own computerized command and control unit CPU8, for at least partly cutting the elastic bands 103, 104, in particular, the elastics present therein, in a coupling zone 105 where the elastic bands 103, 104 are coupled to the respective absorbent pad 101.

The unit 8 comprises a cutting device of substantially known type, not illustrated, provided with at least one cutter driven by the computerized unit CPU8.

The cutter is actuated according to an electronic cam profile based on a control signal S8 generated by the HCPU as a function of the width A and/or of the width D.

Preferably, the processing unit 8 is located downstream of the processing unit 7 in a production feed direction V of the line 1 for the production of the diapers 100.

The elastics of the elastic bands 103, 104 are, for example, cut at the ends of the absorbent pad 101 so as not to tighten it and not affect its absorbent properties.

In an embodiment, for example if the diaper 100 requires it, the processing units of the production line 1 comprise a fourth processing unit 9, provided with its own computerized command and control unit CPU9, for at least partly shaping the elastic bands 103, 104.

The elastic bands 103, 104, for example, may be shaped to enhance the comfort of the diaper 100.

The processing unit 9 comprises a laser or waterjet cutting device driven by the computerized unit CPU9 based on a control signal S9.

The control signal S9 is generated by the HCPU as a function of the length C and/or as a function of the width A and/or as a function of the height B.

The waterjet or laser cutting device allows shaping the product in any way, in particular on the basis of the size of the diaper 100 being produced, as set by the HCPU.

For example, the elastic band 103, 104 used in the production of the diaper 100 has an oversize dimension and is then radiused/trimmed.

In an embodiment, the processing units of the production line 1 or of the assembly line comprise a fifth processing unit 10, provided with its own computerized command and control unit CPU10, for applying a label 106 to the diaper 100; in FIG. 2, the label 106 is drawn with a dashed line because it is optional.

The processing unit 10 comprises an applicator, of known type and not illustrated, for applying the label 106 to each pair of diaper pants 100.

The applicator is driven, for example, by an electronic cam controlled by the unit CPU10, based on a control signal S10.

The control signal S10 is generated by the high level control unit HCPU as a function of the width A so that the label 106 is positioned relative thereto.

The processing unit 10 is preferably located downstream of the processing unit 9 in a production feed direction V of the line 1 for the production of the diapers 100.

In an embodiment, the processing units of the production line 1 or of the assembly line 4 comprise a sixth processing unit 11, provided with its own computerized command and control unit CPU11, for welding the elastic bands 103 in the waist of the product.

The processing unit 11 is located at least downstream of the processing station 7 and downstream of a system, not illustrated, which folds the semi-product 200 in the form of a web comprising the elastic bands 103, 104 and the absorbent pads 101 by 180° so that the elastic bands 103 that will form the waist of the diaper pants 100 are positioned face to face.

In an embodiment, the processing unit 11 comprises a welding device for welding the elastic bands 103 in the waist of the diaper pants 100 and which comprises, for example, a plurality of welding units spaced from each other along a feed path of the diaper pants 100 to be formed.

An example of such a unit is described in document 102019000024712.

The welding units are spaced as a function of the width A and are positioned relative to each other, along the feed path, by the computerized command and control unit CPU11, based on a control signal S11.

The control signal S11 is generated by the control unit HCPU as a function of the width A.

Downstream of the processing unit 11 there is thus a succession of formed diaper pants 100 joined to each other along the lateral welds. Advantageously, using a welding unit that can vary its weld pitch allows making diapers 100 in any size.

In an embodiment, the processing unit 11 comprises a welding device that comprises at least one welder, driven by the computerized unit CPU11 and actuated according to an electronic cam profile based on the control signal S11.

The signal S11 is generated by the control unit HCPU as a function of the width A. By adapting the electronic cam profile to the size being produced, the welding device allows welding diapers 100 of any size.

The processing units of the production line 1, and in particular of the assembly line 4, comprise a seventh processing unit 12, provided with its own computerized command and control unit CPU12, for separating each pair of diaper pants 100 from a succession of diaper pants that are joined to each other.

The processing unit 12 is located downstream of the processing unit 11 in a production feed direction V of the line for the production of the diapers 100 and comprises a fourth cutting device of substantially known type and not illustrated.

The cutting device of the processing unit 12 comprises at least one cutter, driven by the computerized unit CPU12 and actuated according to an electronic cam profile based on a control signal S12.

The control signal S12 is generated by the control unit HCPU as a function of the width A to separate diapers 100 of any size from each other.

The processing units of the production line 1, and in particular of the assembly line 4, comprise an eighth processing unit 13, provided with its own computerized command and control unit CPU13, for spacing and turning the diaper pants 100.

The processing unit 13 is located downstream of the processing unit 12 in the production feed direction V of the line for the production of the diapers 100 to space and turn the diaper pants 100 which have been separated from each other in the processing station 12.

The processing unit 13 comprises a turning and spacing device which comprises at least one rotary means for picking up a pair of diaper pants 100.

The rotary pickup means is driven by the computerized unit CPU13 and is actuated, in its travel, according to an electronic cam profile based on a control signal S13.

The signal S13 is generated by the control unit HCPU as a function of the width A and of the heights B and C.

In practice, the infeed of the processing unit 13 receives an incoming succession of products whose spacing is a function of A and which, at the outfeed, are repositioned according to a spacing that is a function of B and C. Advantageously, in particular by using the electronic cam profile, the processing unit 13 can pick up according to any spacing and return at any spacing, thus adapting to all the possible size variations of diapers 100.

The processing units of the production line 1 and, in particular, of the assembly line 4 comprise a ninth processing unit 14, provided with its own computerized command and control unit CPU14, for folding the elastic bands 103 in the waist of the diaper 100 on the absorbent pad 101.

The waist 103 of the diaper 100 is folded along at least one longitudinal fold line, that is a fold line parallel to the feed direction of the products.

As a function of the width A, the processing unit 14 can also be configured to make two or more folds along longitudinal fold lines.

The processing unit 14 comprises a folding device actuated on the basis of a control signal S14.

The control signal S14 is generated by the control unit HCPU as a function of A and/or as a function of D.

The folding device is preferably an active device and sized to handle elastic bands of any width.

The processing units of the production line 1, and in particular of the assembly line 4, comprise a tenth processing unit 15, provided with its own computerized command and control unit CPU15, for folding at least one absorbent pad 101 of the diaper pants 100.

Folding the absorbent pad 101 occurs along a fold line transverse to the feed direction of the products.

The processing unit 15 comprises a folding device actuated on the basis of a control signal S15.

The control signal S15 is generated by the control unit HCPU as a function of the height A and/or of the length C.

The production line 1, where each processing unit is provided with its own computerized control unit controlled by a single computerized high level control unit HCPU, can, based on input imparted by the latter, adapt production to any required size of diaper 100.

In particular, thanks to their architecture, all the units described comprise operating devices which do not necessitate macroscopic mechanical interventions or, in any case, which do not necessitate human intervention or prolonged machine downtime.

A process for the production of diapers 100 comprises a step of forming a composite web CW to form the composite web CW from which the absorbent pads 101 are obtained. The step of forming the composite web CW is substantially known and not further described.

The process comprises a step of forming elastic bands or strips to form the elastic bands 103, 104 of the diaper 100.

The process comprises a plurality of steps of processing the composite web CW, the elastic bands 103, 104 and semi-products 200 derived from the composite web CW and from the elastic bands 103, 104, as illustrated, for example, in FIG. 4.

The process comprises a step of generating, for each processing step, at least one respective control signal S5, S6, S8, S9, S10, S11, S12, S13, S14, S15 as a function of the size of the diaper pants 100 being produced.

The process comprises a step of adapting each processing step to the size of the diaper pants 100 being produced as a function of the respective control signal.

In an embodiment, at least one control signal is generated as a function of the width D of the absorbent pad 101

In an embodiment, at least one control signal is generated as a function of the length C of the absorbent pad 101.

In an embodiment, at least one control signal is generated as a function of the width A of the waist 103 of the diaper pants 100.

In an embodiment, at least one control signal is generated as a function of the height B of the waist 103 of the diaper pants 100.

In an embodiment, the process comprises a step of cutting the composite web CW to obtain a succession of absorbent pads 101.

The step of cutting the composite web CW is based on a control signal S5 generated as a function of the length 2C of the absorbent pad 101.

In an embodiment, the process comprises a step of turning and spacing to space and turn the absorbent pads 101 of a succession of absorbent pads 101.

The step of turning and spacing the absorbent pads 101 is based on a control signal S6 generated as a function of the width A.

In an embodiment, the process comprises a step of at least partly cutting the elastic bands 103, 104 in a coupling zone 105 where the elastic bands 103, 104 are coupled to the respective absorbent pad 101.

The step of cutting the elastic bands 103, 104 in a coupling zone 105 where the elastic bands 103, 104 are coupled to the respective absorbent pad 101 is based on a control signal S8 generated as a function of the width A.

In an embodiment, the process comprises a step of cutting to at least partly shape the elastic bands 103, 104.

The step of cutting to shape the elastic bands 103, 104 is based on a control signal S9 generated as a function of the length 2C of the absorbent pad 101 and/or as a function of the width A and/or as a function of the height B.

In an embodiment, the step of cutting to shape the elastic bands 103, 104 comprises a step of laser cutting and/or a step of waterjet cutting.

In an embodiment, the process comprises a step of applying a label 106 to each pair of diaper pants 100.

The step of applying is based on a control signal S10 generated as a function of the width A.

In an embodiment, the process comprises a step of welding the elastic bands 103 in the waist of the diaper pants 100 by means of a plurality of welding units.

In an embodiment, the step of welding comprises a step of spacing the welding units along a feed path of the diaper pants 100 to be formed.

The step of spacing is based on a control signal S11 generated as a function of the width A.

In an embodiment, the process comprises a step of cutting to separate each pair of diaper pants 100 from a succession of diaper pants that are joined to each other.

The step of cutting to separate each pair of diaper pants 100 from a succession of diaper pants that are joined to each other is based on a control signal S12 generated as a function of the width A.

In an embodiment, the process comprises a step of turning and spacing to space and turn the diaper pants 100 of a succession of diaper pants 100.

The step of turning and spacing the diaper pants 100 is based on a control signal S13 generated as a function of the width A and/or of the height B and/or of the length 2C.

In an embodiment, the process comprises a step of folding at least one elastic band 103 in the waist of the diaper pants 100.

The step of folding is performed along a longitudinal folding line parallel to a feed direction of the products.

The step of folding is based on a control signal S14 generated as a function of the width A and/or of the width D.

In an embodiment, the process comprises a step of folding to fold the absorbent pad 101 of the diaper pants 100.

The step of folding the absorbent pad 101 is performed along a fold line transverse to a feed direction of the products.

The step of folding the absorbent pad is based on a control signal S15 generated as a function of the height B and/or of the length C.

The following numbered paragraphs set out particular combinations of features considered significant for particular embodiments of this disclosure.

A line (1) for the production of diaper pants (100) of the type each comprising at least one absorbent pad (101) and a plurality of elastic bands (103, 104), said elastic bands (103, 104) and said absorbent pad (101) defining together a pant structure (102), said production line (1) comprising a first forming unit (2) for forming a composite web (CW) from which said absorbent pads (101) are obtained, a second unit (3) for forming elastic bands (103, 104) for forming said elastic bands (103, 104) and an assembly line (4) having a first infeed (4a) for said composite web (CW), a second infeed (4b) for said elastic bands (103, 104) and an outfeed (4c) for said diaper pants (100), said assembly line (4) comprising a plurality of processing units to construct said diaper pants (100) starting at least from said composite web (CW) and from said elastic bands (103, 104), wherein said processing units each comprise a computerized command and control unit and wherein said production line (1) comprises a computerized high level control unit (HCPU) in communication with said computerized control units in the assembly line (4), said high level control unit (HCPU) being configured to impart to each computerized command and control unit at least one control signal for the respective processing unit as a function of the size of the diaper pants (100) being produced in the production line (1), said processing units being configured to perform a respective processing as a function of the size set using the respective control signal.

The production line according to paragraph 1, wherein at least one control signal is a function of the width (D) of the absorbent pad (101).

The production line according to paragraph 1 or 2, wherein at least one control signal is a function of the length (2C) of the absorbent pad (101).

The production line according to any one of the preceding paragraphs, wherein at least one control signal is a function of the width (A) of an elastic band (103) in the waist of the diaper pants (100).

The production line according to any one of the preceding paragraphs, wherein at least one control signal is a function of the height (B) of an elastic band (103) in the waist of the diaper pants (100).

The production line according to any one of the preceding paragraphs, wherein a first processing unit (5) of the plurality of processing units comprises a first cutting device for cutting the composite web (CW) to obtain a succession of absorbent pads (101), said first cutting device comprising at least a first cutter, driven by the computerized unit (CPU5) of the first processing unit (5), and actuated according to an electronic cam profile based on a first control signal (S5), said first control signal (S5) being generated by said high level control unit (HCPU) as a function of the length (20) of the absorbent pad (101).

The production line according to any one of the preceding paragraphs, wherein a second processing unit (6) of the plurality of processing units comprises a first turning and spacing device for spacing and turning the absorbent pads (101) of a succession of absorbent pads, said first turning and spacing device comprising at least a first pickup means for picking up an absorbent pad (101) and a first linear motor for moving said first pickup means, said first linear motor being driven by the computerized command and control unit (CPU6) of the second processing unit (6), and actuated according to an electronic cam profile based on a second control signal (S6), said second control signal (S6) being generated by said high level control unit (HCPU) as a function of the width (A) of an elastic band (103) in the waist of the diaper pants (100).

The production line according to any one of the preceding paragraphs, wherein a third processing unit (8) of the plurality of processing units comprises a second cutting device for at least partly cutting said elastic bands (103, 104) in a coupling zone (105) where the elastic bands (103, 104) are coupled to the respective absorbent pad (101), said second cutting device comprising at least a second cutter, driven by the computerized command and control unit (CPU8) of the third processing unit (8), and being actuated according to an electronic cam profile based on a third control signal (S8), said third control signal (S8) being generated by said high level control unit (HCPU) as a function of the width (A) of an elastic band (103) in the waist of the diaper pants (100) and/or of the width (D) of the absorbent pad (101).

The production line according to any one of the preceding paragraphs, wherein a fourth processing unit (9) of the plurality of processing units comprises a third cutting device for at least partly shaping said elastic bands (103, 104), said third cutting device being a laser or waterjet cutter and being driven by the computerized command and control unit (CPU9) of the fourth processing unit (9) based on a fourth control signal (S9), said fourth control signal (S9) being generated by said high level control unit (HCPU) as a function of the length (2C) of the absorbent pad (101) and/or as a function of the width (A) of an elastic band (103) in the waist of the diaper pants (100) and/or as a function of the height (B) of the elastic band (103) in the waist of the diaper pants (100).

The production line according to any one of the preceding paragraphs, wherein a fifth processing unit (10) of the plurality of processing units comprises an applicator for applying a label (106) to each pair of diaper pants (100), said applicator being driven by the computerized command and control unit (CPU10) of the fifth processing unit (10) based on a fifth control signal (S10), said fifth control signal (S10) being generated by said high level control unit (HCPU) as a function of the width (A) of an elastic band (103) in the waist of the diaper pants (100).

The production line according to any one of the preceding paragraphs, wherein a sixth processing unit (11) of the plurality of processing units comprises a welding device for welding the elastic bands (103) in the waist of the diaper pants (100), said welding device comprising at least one plurality of welding units spaced from each other along a feed path of the diaper pants to be formed, the welding units being spaced as a function of the width (A) of an elastic band (103) in the waist of the diaper pants (100), said welding units being positioned relative to each other, along the feed path, by the computerized command and control unit (CPU11) of the sixth processing unit (11) based on a sixth control signal (S11), said sixth control signal (311) being generated by said high level control unit (HCPU) as a function of the width (A) of an elastic band (103) in the waist of the diaper pants (100).

The production line according to any one of paragraphs 1 to 10, wherein a sixth processing unit (11) of the plurality of processing units comprises a welding device for welding the elastic bands (103) in the waist of the diaper pants (100), said welding device comprising at least one welder being driven by the computerized command and control unit (CPU11) of the sixth processing unit (11) according to an electronic cam profile based on a sixth control signal (S11), said sixth control signal (S11) being generated by said high level control unit (HCPU) as a function of the width (A) of an elastic band (103) in the waist of the diaper pants (100).

The production line according to any one of the preceding paragraphs, wherein a seventh processing unit (12) of the plurality of processing units comprises a fourth cutting device for separating each pair of diaper pants (100) from a succession of diaper pants that are joined to each other, said fourth cutting device comprising at least one fourth cutter driven by the computerized command and control unit (CPU12) of the seventh processing unit (12) and being actuated according to an electronic cam profile based on a seventh control signal (S12), said seventh control signal (S12) being generated by said high level control unit (HCPU) as a function of the width (A) of an elastic band (103) in the waist of the diaper pants (100).

The production line according to any one of the preceding paragraphs, wherein an eighth processing unit (13) of the plurality of processing units comprises a second turning and spacing device for turning and spacing the diaper pants (100) of a succession of diaper pants, said second turning and spacing device comprising at least one second pickup means for picking a pair of diaper pants (100) and being driven by the computerized command and control unit (CPU13) of the eighth processing unit (13) and being actuated according to an electronic cam profile based on an eighth control signal (S13), said eighth control signal (S13) being generated by said high level control unit (HCPU) as a function of the width (A) of an elastic band (103) in the waist of the diaper pants (100) and of the height (B) of the elastic band (103) in the waist of the diaper pants (100).

The production line according to any one of the preceding paragraphs, wherein a ninth processing unit (14) of the plurality of processing units comprises a first folding device for folding an elastic band (103) in the waist of the diaper pants (100), said first folding device being actuated on the basis of a ninth control signal (S14), said ninth control signal (S14) being generated by said high level control unit (HCPU) as a function of the width (A) of an elastic band (103) in the waist of the diaper pants (100) and/or of the width (D) of the absorbent pad (101).

The production line according to any one of the preceding paragraphs, wherein a tenth processing unit (15) of the plurality of processing units comprises a second folding device for folding the absorbent pad (101) of the diaper pants (100), said second folding device being actuated on the basis of a tenth control signal (S15), said tenth control signal (S15) being generated by said high level control unit (HCPU) as a function of the height (B) of an elastic band (103) in the waist of the diaper pants (100) and/or of the length (2C) of the absorbent pad (101).

A process for producing diaper pants (100) of the type each comprising at least one absorbent pad (101) and a plurality of elastic bands (103, 104), said elastic bands (103, 104) and said absorbent pad (101) forming a pants-like structure (102), said process comprising:
- a step of forming a composite web (CW) to form a composite web (CW) from which said absorbent pads (101) are obtained;
- a step of forming elastic strips for forming said elastic bands (103, 104);
- a plurality of steps of processing said composite web (CW), of said elastic bands (103, 104) and of semi-finished items (200) derived from said composite web (CW) and from said elastic bands (103, 104);
- a step of generating, for each processing step, at least one respective control signal as a function of the size of the diaper pants (100) being produced, said process comprising a step of adapting each processing step to the size of the diaper pants (100) being produced as a function of the respective control signal.

The production process according to paragraph 17, wherein at least one control signal is generated as a function of the width (D) of the absorbent pad (101).

The production process according to paragraph 17 or 18, wherein at least one control signal is generated as a function of the length (2C) of the absorbent pad (101).

The production process according to any of the paragraphs from 17 to 19, wherein at least one control signal is generated as a function of the width (A) of an elastic band (103) in the waist of the diaper pants (100).

The production process according to any of the paragraphs from 17 to 20, wherein at least one control signal is generated as a function of the height (B) of an elastic band (103) in the waist of the diaper pants (100).

The production process according to any of the paragraphs from 17 to 21, comprising a first step of cutting said composite web (CW) to obtain a succession of absorbent pads, said first step of cutting being performed on the basis of a first control signal (S5) generated as a function of the length (2C) of the absorbent pad (101).

The production process according to any of the paragraphs from 17 to 22, comprising a step of turning and spacing to space and turn the absorbent pads (101) of a succession of absorbent pads, said step of turning and spacing being performed on the basis of a second control signal (S6), generated as a function of the width (A) of an elastic band (103) in the waist of the diaper pants (100).

The production process according to any of the paragraphs from 17 to 23, comprising a second step of cutting at least partly the elastic bands (103, 104) in a coupling zone (105) where the elastic bands (103, 104) are coupled to the respective absorbent pad (101), said second step of cutting being performed on the basis of a third control signal (S8), generated as a function of the width (A) of an elastic band (103) in the waist of the diaper pants (100).

The production process according to any of the paragraphs from 17 to 24, comprising a third step of cutting to at least partly shape the elastic bands (103, 104), said third step of cutting being performed on the basis of a fourth control signal (S9), generated as a function of the length (2C) of the absorbent pad (101), and/or as a function of the width (A) of an elastic band (103) in the waist of the diaper pants (100) and/or as a function of the height (B) of the elastic band (103) in the waist of the diaper pants (100).

The production process according to paragraph 25, wherein the third step of cutting comprises a step of laser cutting and/or a step of waterjet cutting.

The production process according to any of the paragraphs from 17 to 26, comprising a step of applying a label (106) to each pair of diaper pants (100), said step of applying being performed on the basis of a fifth control signal (S10), generated as a function of the width (A) of an elastic band (103) in the waist of the diaper pants (100).

The production process according to any of the paragraphs from 17 to 27, comprising a step of welding the elastic bands (103) in the waist of the diaper pants (100) by means of a plurality of welding units, said step of welding comprising a step of spacing the welding units along a feed path of the diaper pants (100) to be formed, said step of spacing being performed on the basis of a sixth control signal (S11), generated as a function of the width (A) of an elastic band (103) in the waist of the diaper pants (100).

The production process according to any of the paragraphs from 17 to 28, comprising a fourth step of cutting to separate each pair of diaper pants (100) from a succession of diaper pants that are joined to each other, said fourth step of cutting being performed on the basis of a seventh control signal (S12), generated as a function of the width (A) of an elastic band (103) in the waist of the diaper pants (100).

The production process according to any of the paragraphs from 17 to 29, comprising a second step of turning and spacing to space and turn the diaper pants (100) of a succession of diaper pants, said second step of turning and spacing being performed on the basis of an eighth control signal (S13), generated as a function of the width (A) of an elastic band (103) in the waist of the diaper pants (100) and of the height (B) of the elastic band (103) in the waist of the diaper pants (100).

The production process according to any of the paragraphs from 17 to 30, comprising a first step of folding to fold at least one elastic band (103) in the waist of the diaper pants (100), said first step of folding being performed on the basis of a ninth control signal (S14), generated as a function of the width (A) of an elastic band (103) in the waist of the diaper pants (100) and/or as a function of the width (D) of the absorbent pad (101).

The production process according to any of the paragraphs from 17 to 31, comprising a second step of folding to fold the absorbent pad (101) of the diaper pants (100), said second step of folding being performed on the basis of a tenth control signal (S15), generated as a function of the height (B) of an elastic band (103) in the waist of the diaper pants (100) and/or as a function of the length (2C) of the absorbent pad (101).

What is claimed is:

1. A line for production of diaper pants each comprising at least one absorbent pad and a plurality of elastic bands, said elastic bands and said at least one absorbent pad defining together a pant structure, said production line comprising:
   - a first forming unit for forming a composite web from which said at least one absorbent pad is obtained,
   - a second unit for forming elastic bands for forming said elastic bands and an assembly line having a first infeed for said composite web, a second infeed for said elastic bands and an outfeed for said diaper pants,
   - said assembly line comprising a plurality of processing units to construct said diaper pants starting from said composite web and from said elastic bands,
   - wherein said processing units each comprise a computerized command and control unit and wherein said production line comprises a computerized high level control unit in communication with said computerized control units in the assembly line,
   - said high level control unit being configured to impart to each computerized command and control unit at least one control signal adapting production operation of the respective processing unit as a function of a size of the diaper pants being produced in the production line, said processing units being configured to perform a respective processing as a function of a format set using the respective at least one control signal;

wherein the plurality of processing units include:
- a processing unit configured for cutting the composite web;
- a processing unit configured for spacing and rotating the absorbent pads;
- a processing unit configured for cutting the elastic bands;
- a processing unit configured for applying a label to the diaper pants;
- a processing unit configured for welding the elastic bands to the diaper pants;
- a processing unit configured for separating the diaper pants from each other; and
- a processing unit configured for spacing the diaper pants;
- wherein each of the processing units uses electronic cam profiles to provide for complete adaptability of the line regardless of a size of the diaper pants, or a subcomponent thereof, wherein each of the electronic cam profiles is driven by a respective at least one control signal.

2. The production line according to claim 1, wherein the at least one control signal is a function of a width of the at least one absorbent pad.

3. The production line according to claim 1, wherein the at least one control signal is a function of a length of the at least one absorbent pad.

4. The production line according to claim 1, wherein the at least one control signal is a function of a width of one of the elastic bands in a waist of the diaper pants.

5. The production line according to claim 1, wherein the at least one control signal is a function of a height of one of the elastic bands in a waist of the diaper pants.

6. A process for producing diaper pants each comprising at least one absorbent pad and a plurality of elastic bands, said elastic bands and said at least one absorbent pad forming a pants structure, said process comprising:
- a step of forming a composite web from which said at least one absorbent pad is obtained;
- a step of forming elastic strips for forming said elastic bands;
- a plurality of steps of processing said composite web, of said elastic bands and of semi-finished items derived from said composite web and from said elastic bands;
- a step of generating, for each of the processing steps, at least one respective control signal setting a format for controlling production operation of the respective processing step as a function of a size of the diaper pants being produced,
- a step of adapting each of the processing steps to the size of the diaper pants being produced as a function of the format set using the at least one respective control signal;
- providing a plurality of processing units that include:
  - a processing unit configured for cutting the composite web;
  - a processing unit configured for spacing and rotating the absorbent pads;
  - a processing unit configured for cutting the elastic bands;
  - a processing unit configured for applying a label to the diaper pants;
  - a processing unit configured for welding the elastic bands to the diaper pants;
  - a processing unit configured for separating the diaper pants from each other; and
  - a processing unit configured for spacing the diaper pants;
  - wherein each of the processing units uses electronic cam profiles to provide for complete adaptability of the process regardless of a size of the diaper pants, or a subcomponent thereof, wherein each of the electronic cam profiles is driven by a respective at least one control signal.

7. The production process according to claim 6, wherein the at least one respective control signal is generated as a function of a width of the at least one absorbent pad.

8. The production process according to claim 6, wherein the at least one respective control signal is generated as a function of a length of the at least one absorbent pad.

9. The production process according to claim 6, wherein the at least one respective control signal is generated as a function of a width of one of the elastic bands in a waist of the diaper pants.

10. The production process according to claim 6, wherein the at least one respective control signal is generated as a function of a height of one of the elastic bands in a waist of the diaper pants.

* * * * *